United States Patent
Kamal

(10) Patent No.: US 10,350,256 B2
(45) Date of Patent: *Jul. 16, 2019

(54) COMPOSITIONS FOR THE TREATMENT OF DERMATOLOGICAL CONDITIONS, DISORDERS OR DISEASES

(71) Applicant: Veit Hoermann Gesellschaft Für Unternehmenskommunikation mbH, Berlin (DE)

(72) Inventor: Thaher Kamal, Berlin (DE)

(73) Assignee: Veit Hoermann Gesellschaft Für Unternehmenskommunikation mbH (DE)

( * ) Notice: Subject to any disclaimer, the term of this patent is extended or adjusted under 35 U.S.C. 154(b) by 235 days.

This patent is subject to a terminal disclaimer.

(21) Appl. No.: 15/437,648

(22) Filed: Feb. 21, 2017

(65) Prior Publication Data

US 2017/0189466 A1  Jul. 6, 2017

Related U.S. Application Data

(63) Continuation of application No. 14/654,342, filed as application No. PCT/EP2013/003822 on Dec. 18, 2013, now Pat. No. 9,675,655.

(30) Foreign Application Priority Data

Dec. 19, 2012 (EP) .................................. 12008448

(51) Int. Cl.
| | |
|---|---|
| A61K 36/00 | (2006.01) |
| A61K 36/71 | (2006.01) |
| A61K 31/23 | (2006.01) |
| A61K 36/61 | (2006.01) |
| A61K 36/185 | (2006.01) |
| A61K 36/63 | (2006.01) |
| A61K 9/00 | (2006.01) |
| A61K 9/06 | (2006.01) |
| A61K 31/07 | (2006.01) |
| A61K 31/355 | (2006.01) |
| A61K 31/59 | (2006.01) |
| A61K 31/714 | (2006.01) |

(52) U.S. Cl.
CPC .......... *A61K 36/71* (2013.01); *A61K 9/0014* (2013.01); *A61K 9/06* (2013.01); *A61K 31/07* (2013.01); *A61K 31/23* (2013.01); *A61K 31/355* (2013.01); *A61K 31/59* (2013.01); *A61K 31/714* (2013.01); *A61K 36/185* (2013.01); *A61K 36/61* (2013.01); *A61K 36/63* (2013.01)

(58) Field of Classification Search
CPC ....................................................... A61K 36/00
USPC .......................................................... 424/725
See application file for complete search history.

(56) References Cited

U.S. PATENT DOCUMENTS

| | | |
|---|---|---|
| 2002/0132019 A1 | 9/2002 | Kandil |
| 2003/0060508 A1 | 3/2003 | Kandil |
| 2006/0083708 A1 | 4/2006 | Schwartz |
| 2007/0207115 A1 | 9/2007 | Liegeois |
| 2007/0281044 A1 | 12/2007 | Mueller et al. |
| 2008/0107758 A1 | 5/2008 | Crutchfield, III |
| 2011/0076346 A1 | 3/2011 | Babish et al. |

FOREIGN PATENT DOCUMENTS

| | | |
|---|---|---|
| CN | 101829074 A | 9/2010 |
| RU | 2233152 C1 | 7/2004 |
| WO | 00/32211 A1 | 6/2000 |
| WO | 2010/018526 A2 | 2/2010 |
| WO | 2011/148257 A2 | 12/2011 |

OTHER PUBLICATIONS

Kalus et al., "Effect of *Nigella sativa* (black seed) on subjective feeling in patients with allergic diseases," Phytotherapy Research, vol. 17, Jan. 1, 2003, pp. 1209-1214.

Abu-Al-Basal, Mariam A., "Influence of *Nigella sativa* fixed oil on some blood parameters and histopathology of skin in staphylococcal-infected BALB/c mice," Pakistan journal of biological sciences: PJBS, Dec. 1, 2011, 14:1038, Abstract Only.

*Primary Examiner* — Michael V Meller
(74) *Attorney, Agent, or Firm* — McDonnell Boehnen Hulbert & Berghoff LLP

(57) ABSTRACT

The present invention relates to compositions comprising black cumin (*Nigelia sativa* seed) oil, olive oil, tea tree (*Melaleuca alternifolia*) oil, cocoa butter, vitamin A or a derivative thereof, and vitamin B12 or a derivative thereof. The compositions of the present invention can be advantageously used in the in the treatment of dermatological conditions, disorders or diseases, in particular inflammatory dermatological diseases such as psoriasis.

4 Claims, 15 Drawing Sheets

COMPOSITIONS FOR THE TREATMENT OF DERMATOLOGICAL CONDITIONS, DISORDERS OR DISEASES

CROSS-REFERENCE

This application is a continuation of U.S. patent application Ser. No. 14/654,342, filed Jun. 19, 2015, now U.S. Pat. No. 9,675,655, issued Jun. 13, 2017, which is a section 371 National phase of international application no. PCT/EP/2013/003822, filed Dec. 18, 2013, which claims priority from European patent application no. EP 12008448, filed Dec. 19, 2012, which are incorporated by reference in their entirety.

FIELD

The present invention relates to compositions comprising black cumin (*Nigella sativa* seed) oil, olive oil, tea tree (*Melaleuca alternifolia*) oil, cocoa butter, vitamin A or a derivative thereof, and vitamin B12 or a derivative thereof. The compositions of the present invention can be advantageously used in the in the treatment of dermatological conditions, disorders or diseases, in particular inflammatory dermatological diseases such as psoriasis.

BACKGROUND

The human skin is the outer covering and a metabolically active organ of the human body. It is the largest organ of the integumentary system with a surface area of about 1.8 square meters in a grown adult. The skin is composed of three layers of ectodermal tissue, guards the underlying muscles, bones, ligaments and internal organs, and maintains inner homeostasis. Since it interfaces with the environment, the skin plays a key role in protecting the body against pathogens. Accordingly, almost all types of cells of the immune system can be found within the skin that can inter alia mediate a variety of allergic reactions that occur at or within the skin. The range of known skin or dermatological diseases is broad, wherein the most common include psoriasis, eczema, acne and Herpes simplex infections. In all dermatological diseases, factors such as nutrition, hygiene, UV exposure, climate, complexion, sex, age, and genetic determinants, as well as stress and psychological factors play a more or less prominent role.

Psoriasis is a chronic, non-infectious, inflammatory disease of the skin. It is characterized by sharply bounded plaques with a silvery-white scaling. The clinical picture of psoriasis is very broad, reaching from mild alterations of the skin to life-threatening systemic conditions. In over a third of the affected patients, a genetic predisposition can be determined. The disease can further be provoked or aggravated by factors such as trauma, infections, exposure to UV radiation, stress, artificial food products, alcohol, smoking, or various medicaments. Sometimes, psoriasis is accompanied by joint disorders or autoimmune conditions. Treatment of psoriasis commonly uses topical medicaments such as tar preparations, dithranol, corticosteroids, vitamin D analogues, or salicylic acid. More severe forms of the disease often have to be treated systemically using photochemical therapies, retinoids, methotrexate, hydroxyurea, azathioprine or cyclosporin. However, some of these have severe side-effects and/or are not effective in some patients. Recently, clinical studies using monoclonal antibodies or certain fusion proteins have been conducted, showing improved efficacy against psoriasis. However, the pharmacological safety of such treatments remains to be shown. In summary, treatments of more severe forms of psoriasis are costly, often show undesirable side-effects, and have a varying efficacy.

Eczemas are non-infectious, inflammatory skin diseases that can be caused by a wide range of stimuli. They are classified as exogenous eczemas, endogenous eczemas and non-classifiable eczemas. The most common exogenous eczema is known as contact dermatitis which can be caused by various substances such as chrome, cobalt, dermal patches, softening agents, lacquers, finishers, impregnating agents, adhesives, fragrances, nickel, colors and others. The treatment of contact eczema is very difficult, as long as the aggrieving allergen is not found and eliminated. Accordingly, identification of the allergen is of paramount importance. During the acute phase, corticosteroidal ointments can be used. The most common endogenous eczema is atopic eczema, also known as atopic dermatitis or neurodermitis. Atopic eczema is a chronic inflammation of the skin that is often associated with asthma, allergic rhinitis and/or conjunctivitis. Some studies suggest an involvement of allergic reactions to house dust mites and certain substances. The disease pattern is broadly diversified and symptoms are frequently regressing and recurring. Treatment of atopic eczema involves the elimination of the eliciting factor, e.g. house dust mites, animal hair, wool and other irritants, as well as the use of skin care agents, topical steroids, oral antibiotics or dietary measures. Recently, two new immunosuppressive macrolides, tacrolimus and pimecrolimus, have been investigated. Both are used topically and show a similar mechanism of action. In severe forms of atopic eczema, phototherapy, photochemotherapy, and systemic immunosuppressives such as cyclosporin A are used.

Acne is caused by inflammation of sebaceous glands. It is characterized by an increased production of sebum and a colonization of sebaceous gland ducts by bacteria. There exists a huge variety of cosmetic and pharmacological products for the treatment of acne that are applied topically. In severe forms of acne, medicaments such as antibiotics, antiandrogens, retinoids and others can be used.

Herpes simplex is an acute viral infection that is transmitted via infected subjects and can occur at various sites such as the mouth or the genitals. The disease cycles between active periods and periods of remission, wherein reactivation is mediated by factors such as e.g. stress. As no cure for herpes has been found so far, the virus persists in the body for life. Treatment of herpes involves the topical application of aciclovir-containing creams which have been shown to be able to shorten the disease periods.

Recently, it has been shown that oxidative stress plays a major role in the development and maintenance of dermatological diseases, in particular inflammatory diseases such as the ones indicated above. During normal metabolism, an adult human uses about 250 grams of oxygen per day. About 2 to 5% of this amount are converted to reactive oxygen species (ROS). These are short-lived but highly reactive molecules that have a normal physiological role in low concentrations, but can severely damage cells in higher concentrations. Therefore, the accumulation of ROS is prevented by cellular anti-oxidative systems that maintain the so-called redox-homeostasis. However, any disturbance of this homeostasis due to an increased formation of ROS and/or a decreased activity of the anti-oxidative systems can lead to oxidative stress. Oxidative stress in turn can lead to DNA damage, peroxidation of lipids, and damage of cell membranes, as well as to inflammatory immune reactions by the induction of inflammatory cytokines that are related to the pathogenesis of various inflammatory skin diseases including psoriasis, atopic dermatitis, acne and others.

In summary, dermatological diseases, in particular inflammatory diseases, pose a serious and often chronic impairment of the quality of life of the affected subjects and in extreme cases can even lead to life-threatening conditions. Many of these diseases can only be treated in a symptomatic manner, wherein treatments are often not very effective. Further, more severe cases often require the treatment with medicaments that have severe side-effects.

SUMMARY

Accordingly, the technical problem underlying the present invention is to provide improved means for the treatment of skin diseases, in particular inflammatory skin diseases. These means should be efficient in a broad range of diseases, lead to a substantial amelioration of the symptoms or even a cure of the disease, and have no or only mild side-effects.

The solution to the above technical problem is achieved by the embodiments characterized in the claims.

DETAILED DESCRIPTION

Figure 1:
FIG. 1 shows the neck area of a female patient suffering from atopic eczema since her birth after continuous treatment with a composition according to the present invention (Recipe N).

In particular, in a first aspect, the present invention relates to a composition comprising black cumin (*Nigella sativa* seed) oil, olive oil, tea tree (*Melaleuca alternifolia*) oil, cocoa butter, at least one of vitamin A or a derivative thereof and vitamin E or a derivative thereof, and at least one of vitamin B12 or a derivative thereof and vitamin D or a derivative thereof.

Black cumin oil is an oil that is obtained from the seeds of *Nigella sativa* which is an annual flowering plant native to south and southwest Asia. The seeds are known as black cumin and are often used as a spice in said regions. Further, black cumin oil has been traditionally used as a remedy for a wide range of ailments. The essential oil components of black cumin oil are thymoquinones which have been shown to have anti-oxidative, anti-inflammatory, anti-proliferative, anti-allergic and anti-bacterial activities, as well as immunomodulatory and immunotherapeutic characteristics. All types of black cumin oil can be used in the composition of the present invention, and methods for the production of black cumin oil are known in the art.

Olive oil contains a high concentration of polyphenols, in particular hydroxytyrosol and derivatives thereof. Further, olive oil contains various unsaturated fatty acids. Just like black cumin oil, olive oil has been shown to have anti-oxidative, anti-inflammatory, and anti-microbial activities. However, the mechanism of action of olive oil is different from that of black cumin oil. All types of olive oil can be used in the composition of the present invention. Methods for the production of olive oil are known in the art.

Tea tree oil is an oil that is obtained from the leaves of *Melaleuca alternifolia* which is a tree that is native to southeast Queensland and the northeast coast of New South Wales, Australia. Tea tree oil is mainly composed of various terpinens, in particular terpinen-4-ol. It has anti-oxidative and anti-inflammatory activities and has been traditionally used in the treatment of a wide range of diseases including bacterial, viral, fungal and protozoal infections. All types of tea tree oil can be used in the composition of the present invention, and methods for the production thereof are known in the art.

Cocoa butter is an edible vegetable fat extracted from cocoa beans. It has a high content of saturated fats derived from stearic and palmitic acids that pose a low risk of heart diseases and arteriosclerose. Further, it contains various anti-oxidants that are related to catechines and epicatechines, as well as others that are related to procyanidines and polyphenols. All types of cocoa butter can be used in the composition of the present invention. Methods for the production of cocoa butter are known in the art.

Vitamin A has anti-oxidative activity and is one if the cells physiological anti-oxidants. It has been used orally and topically in the treatment of psoriasis. The term "vitamin A or a derivative thereof" as used herein includes all forms of vitamin A and any compounds that have vitamin A activity. In particular, said term includes all compounds having a beta-ionone ring to which a retinyl group is attached, both structural features that are essential for vitamin A activity. Example given, the term "vitamin A or a derivative thereof" includes retinol, retinal, retinyl palmitate, retinyl acetate, retinoic acid, retinoids, beta-carotene, alpha-carotene, gamma-carotene, beta-cryptoxanthene, and retinyl esters.

Vitamin E acts as an antioxidant, regulator of enzymatic activity, and regulator of gene expression. The term "vitamin E or a derivative thereof" as used herein includes all forms of vitamin E and any compounds that have vitamin E activity. In particular, said term includes the tocopherols alpha-, beta-, gamma-, and delta-tocopherol, as well as the tocotrienols alpha-, beta-, gamma-, and delta-tocotrienol.

Vitamin B12 is a water-soluble vitamin with a key role in the normal functioning of the brain and nervous system, as well as for the formation of blood. It affects inter alia DNA synthesis and regulation, fatty acid synthesis and energy production. The term "vitamin B12 or a derivative thereof" as used herein includes all forms of vitamin B12 and any compounds that have vitamin B12 activity. In particular, said term includes cobalamin, hydroxycobalamin, cyanocobalamin, methylcobalamin, adenosylcobalamin, 5'-deoxyadenosyl-cobalamin, aquocobalamin, and nitritocobalamin.

Vitamin D is a hormone belonging to the group of fat-soluble secostreoids. It is responsible for intestinal absorption of calcium and phosphate. The active principle of vitamin D is synthesized from cholesterol in the liver and kidney when exposure to sunlight is adequate. Under such circumstances, no vitamin D supplementation is needed. Vitamin D helps in maintaining calcium homeostasis and bone resorption. Further, it has an effect on immune cells such as monocytes and activated T and B lymphocytes. Moreover, it acts as an antioxidant. The term "vitamin D or a derivative thereof" as used herein includes all forms of vitamin D and any compounds that have vitamin D activity. In particular, said term includes vitamin $D_1$, vitamin $D_2$ (ergocalciferol), vitamin $D_3$ (cholecalciferol), and vitamin $D_4$ (22-dihydroergocalciferol), and vitamin $D_5$ (sitocalciferol).

In a preferred embodiment, the composition of the present invention comprises vitamin A or a derivative thereof and vitamin B12 or a derivative thereof.

In a preferred embodiment, the composition of the present invention comprises at least one of its components in the following amounts:
black cumin oil in an amount of from 8 to 12% (w/w),
olive oil in an amount of from 8 to 12% (w/w),
tea tree oil in an amount of from 0.07 to 0.10% (w/w),
cocoa butter in an amount of from 1 to 6% (w/w),
vitamin A or a derivative thereof in an amount of from 0.02 to 0.06% (w/w),
vitamin E or a derivative thereof in an amount of from 0.02 to 0.06% (w/w),
vitamin B12 or a derivative thereof in an amount of from 0.02 to 0.06% (w/w), and
vitamin D or a derivative thereof in an amount of from 0.02 to 0.06% (w/w), with respect to the total weight of the composition.

Preferably, all of the components of the composition of the present invention are comprised therein in the amounts as given above.

In a more preferred embodiment, the composition of the present invention comprises at least one of its components in the following amounts:
black cumin oil in an amount of 11% (w/w),
olive oil in an amount of 11% (w/w),
tea tree oil in an amount of 0.09% (w/w),
cocoa butter in an amount of 4% (w/w),
vitamin A or a derivative thereof in an amount of 0.05% (w/w),
vitamin E or a derivative thereof in an amount of 0.05% (w/w),
vitamin B12 or a derivative thereof in an amount of 0.05% (w/w), and
vitamin D or a derivative thereof in an amount of 0.05% (w/w),
with respect to the total weight of the composition.

Preferably, all of the components of the composition of the present invention are comprised therein in the amounts as given above.

In preferred embodiments, the composition of the present invention further comprises one or more components selected from the group consisting of pharmaceutically and/or cosmetically acceptable excipients, solvents, preservatives, antioxidants, thickening agents, gelling agents, surfactants, emollients, emulsifiers, oil bases, ointment bases, penetration enhancers, solubilizers, chelating agents, fragrances and buffering agents. Respective compounds are not particularly limited and are known in the art. A particular example of a pharmaceutically and/or cosmetically acceptable solvent is water. Particular examples of oil bases or ointment bases are (i) the so-called Basiscreme DAC (base cream according to the German pharmaceuticals code), containing 4% (w/w) glycerol monostearate 60, 6% (w/w) cetyl alcohol, 7.5% (w/w) mid-chain triglycerides, 25.5% (w/w) white petrolatum, 7% (w/w) macrogol-20-glycerol monostearate, 10% (w/w) propylene glycol, and 40% (w/w) purified water, and (ii) Eucerinum anhydricum, containing 6% (w/w) lanolin alcohols, 0.5% (w/w) cetylstearyl alcohol, and 93.5% (w/w) white petrolatum.

Preferably, the composition of the present invention is for topical administration, i.e. it is formulated to be suitable for topical administration. Preferably, the composition of the present invention is in the form of a cream, a lotion, an ointment, a gel, an emulsion, a solution or a dermal patch, wherein a cream is particularly preferred. Methods for the formulation of the compositions of the present invention as a cream, a lotion, an ointment, a gel, an emulsion, a solution or a dermal patch are not particularly limited and are known in the art.

In preferred embodiments, the compositions of the present invention are for use in medicine. More preferably, said compositions are for use in the treatment of a dermatological condition, disorder or disease in a subject in need thereof. Said dermatological condition, disorder or disease is preferably an inflammatory dermatological condition, disorder or disease. In specific embodiments, the dermatological condition, disorder or disease is selected from the group consisting of psoriasis, neurodermitis, atopic dermatitis, atopic eczema, acne, herpetic infection of the skin, warts, and herpes zoster, wherein psoriasis and atopic eczema are particularly preferred. Preferably, the subject is a human.

In a second aspect, the present invention relates to the use of a composition according to the present invention as a cosmetic. In this aspect, the composition can be any composition as defined above.

The present invention has been realized based on the finding that different plants and plant extracts have been traditionally used for a long time by many peoples for the treatment of various ailments. In the meantime it has been shown that many of these plants or plant extract contain highly efficient anti-inflammatory, anti-microbial, anti-allergic and analgetic agents. In the present invention, it has been found that compositions containing specific natural or naturally derived substances provide a highly efficient means for the treatment of various dermatological diseases, in particular inflammatory dermatological diseases. The substances comprised in the compositions of the present invention synergistically provide a therapeutic effect that is not based on singular substances, but on a synergistic combination of various prophylactic, therapeutic, anti-inflammatory, immunological and anti-microbial activities.

The present invention will now be further illustrated in the following examples without being limited thereto.

EXAMPLES

Example 1

Preparation of a Composition According to the Present Invention (Recipe N)

A composition according to the present invention was prepared according to the following formulation (Recipe N):

| No. | Compound | Amount | Amount [kg] | Amount [% (w/w)] |
|---|---|---|---|---|
| 1 | Water (low-germ, de-ionized) | 12 liters | 12 | 12 |
| 2 | Basiscreme DAC | 44.81 kg | 44.81 | 44.81 |
| 3 | Eucerinum anhydricum | 17 kg | 17 | 17 |
| 4 | Olive oil (refined) PhEur. | 12 liters | 11 | 11 |
| 5 | Black cumin oil | 12 liters | 11 | 11 |
| 6 | Cocoa butter | 4 kg | 4 | 4 |
| 7 | Vitamin B12 Cya. 0.1% SD | 0.05 kg | 0.05 | 0.05 |
| 8 | Vitamin A (retinyl palmitate) 1.0 million IU/g | 0.05 kg | 0.05 | 0.05 |
| 9 | Tea tree oil | 100 ml | 0.09 | 0.09 | total quantity 100 kg

The composition was prepared according to the following procedure:
Pre-Preparation:
1. add vitamin B12 to 1 liter of water
Mode of Preparation:
1. melt Eucerinum anhydricum at 37° C.
2. add olive oil and black cumin oil
3. mix for app. 5 min with app. 1000 rpm, without pressure
4. add cocoa butter and mix additional 5 min
5. add vitamin A and tea tree oil and mix for additional 5 min
6. add Basiscreme DAC and mix for additional 10 min at 1500 rpm
7. change temperature to 20° C. and change pressure to 1 bar, then add water and vitamin B12/water and mix for additional 20 min at 1500 rpm
8. mix for additional 5 min at 2000 rpm, 1 bar pressure, 20° C. temperature
9. direct filling & distribution into packaging (tubes, or similar)

Example 2

Preparation of a Composition According to the Present Invention (Recipe P)

A composition according to the present invention was prepared according to the following formulation (Recipe P):

| No. | Compound | Amount [kg] | Amount [% (w/w)] |
|---|---|---|---|
| 1 | Water (low-germ, de-ionized) | 15.9 | 15.9 |
| 2 | Eucerinum anhydricum | 49 | 49 |
| 3 | Olive oil (refined) PhEur. | 9.4 | 9.4 |
| 4 | Black cumin oil | 9.4 | 9.4 |
| 5 | Cocoa butter | 1.2 | 1.2 |
| 6 | Vitamin B12 Cya. 0.1% SD | 0.036 | 0.036 |
| 7 | Vitamin A (retinyl palmitate) 1.0 million IU/g | 0.032 | 0.032 |
| 8 | Tea tree oil | 0.032 | 0.032 | total quantity 100 kg

The composition was prepared according to the following procedure:
Pre-Preparation:
1. add vitamin B12 to 1 liter of water
Mode of Preparation:
1. melt Eucerinum anhydricum at 37° C.
2. add olive oil and black cumin oil
3. mix for app. 5 min with app. 1000 rpm, without pressure
4. add cocoa butter and mix additional 5 min
5. add vitamin A and tea tree oil and mix for additional 5 min
6. mix for additional 10 min at 1500 rpm
7. change temperature to 20° C. and change pressure to 1 bar, then add water and vitamin B12/water and mix for additional 20 min at 1500 rpm
8. mix for additional 5 min at 2000 rpm, 1 bar pressure, 20° C. temperature
9. direct filling & distribution into packaging (tubes, or similar)

Example 3

Dermal Compatibility of a Composition According to the Present Invention (Recipe The composition of Example 1 (Recipe N) has been tested for its dermal compatibility in a patch test. Said patch test is a standardized dermatological examination to check the compatibility of preparations to be used on the human skin. The examination was carried out according to the recommendations of the expert group of COLIPA (European organization of the cosmetic, toiletry and perfumery industry) in vivo at 30 subjects.

The examination did not show evidence of possible incompatibilities of the composition to the human skin considering the conditions of use. Therefore, the skin compatibility of the composition has been assessed as good.

Example 4

Preservation Efficacy of a Composition According to the Present Invention (Recipe N)

The composition of Example 1 (Recipe N) has been challenged with various microorganisms. In particular, 40 g of the composition were inoculated with 200 µl of a suspension containing about $10^8$ cfu/ml of *Staphylococcus aureus, Pseudomonas aeruginosa*, and *Escherichia coli*, or with 200 µl of a suspension containing about $10^7$ to $10^8$ cfu/ml of *Candida albicans* and *Aspergillus niger*.

Samples were incubated at room temperature in the dark for up to four weeks. The results are shown in the Table below.

|  | cfu/g after day | | | | | |
| --- | --- | --- | --- | --- | --- | --- |
|  | 0 | 2 | 7 | 14 | 21 | 28 |
| *Staphylococcus aureus* | 750.000 | <100 | <100 | <100 | <100 | <100 |
| *Pseudomonas aeruginosa* | 750.000 | | | | | |
| *Escherichia coli* | 750.000 | | | | | |
| *Aspergillus niger* | 150.000 | 20.000 | 15.000 | 14.000 | 13.600 | 10.000 |
| *Candida albicans* | 750.000 | 100.000 | 90.000 | 63.000 | 56.000 | 40.000 |

According to the above data, the composition has been assessed as being sufficiently preserved.

Example 5

Storage Stability of a Composition According to the Present Invention (Recipe N)

Quantities of the composition of Example 1 (Recipe N) have been stored for one month at room temperature and at 40° C. The composition was determined to be stable at both conditions as far as emulsion, fragrance and color are concerned. Accordingly, it has been estimated that the composition is stable for over 30 month of storage.

Example 6

Case Reports

Various patients have been treated topically with one of the compositions of Example 1 (Recipe N) and Example 2 (Recipe P). These patients were therapy-refractory, i.e. the patients had already been treated with standard therapies to no avail. All patients treated with the compositions of the present invention showed significant ameliorations of the symptoms or even complete remission without any negative side-effects. Since the patients had been suffering from their respective diseases for a long time, the treatment with the compositions of the present invention seems to be effective in all stages of the diseases.

Patient A:

A 21 years old female patient suffering from atopic eczema for all her life received a continuous treatment of the affected body parts (elbows, neck, face, legs) over one month with the composition of Example 1 (Recipe N) in an amount of 1 to 10 grams in two treatments per day. The treatment resulted in a significant amelioration of the symptoms (FIG. 1).

Figure 2:
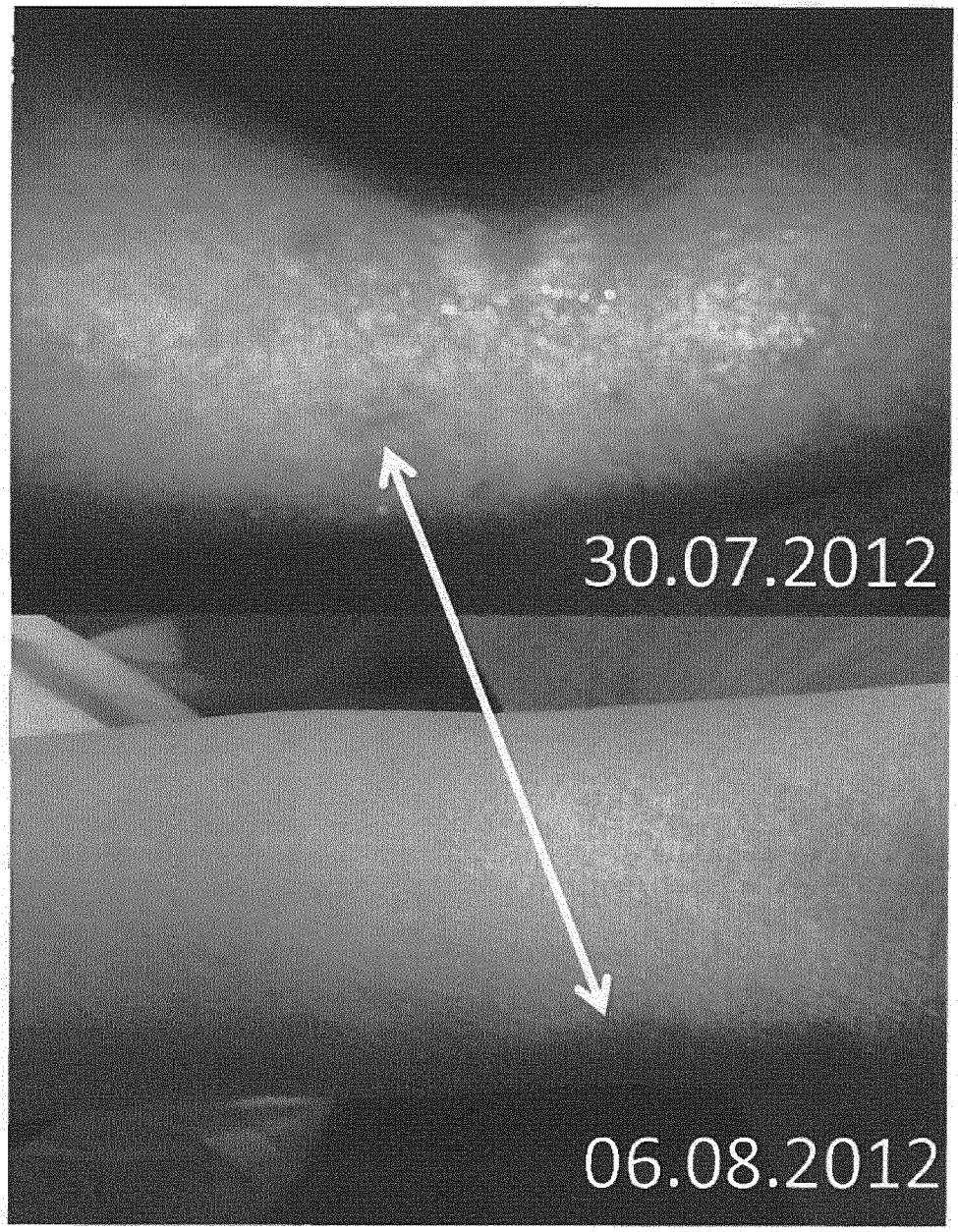
FIG. 2A shows the elbow area of a female patient suffering from atopic eczema for more than 20 years before and after one week of treatment with a composition according to the present invention (Recipe N).
FIG. 2B shows the neck area of a female patient suffering from atopic eczema for more than 20 years before and after one week of treatment with a composition according to the present invention (Recipe N).
Figure 2:
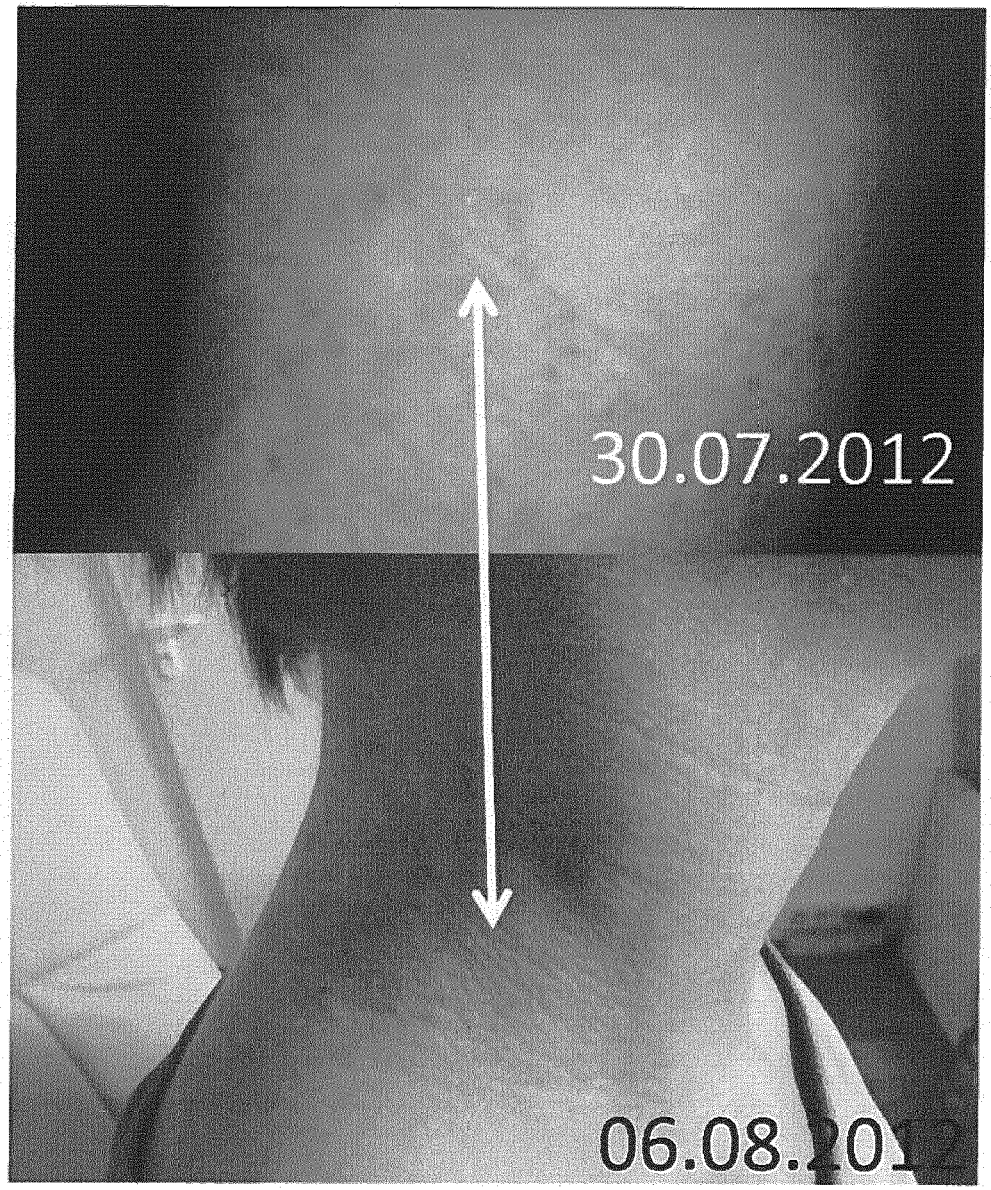

Patient B:

A 32 years old female patient suffering from atopic eczema for more than 20 years received a treatment of the affected body parts (elbows, neck, face) with the composition of Example 1 (Recipe N) for two weeks in an amount of 3 grams in two treatments per day. The patient had already tried several conventional therapies, including cortisone treatment, without any success. The treatment with the composition of the present invention resulted in a significant amelioration of the symptoms (FIGS. 2 A and 2B). The patient stated that she had never felt so good in 20 years.

Figure 3:
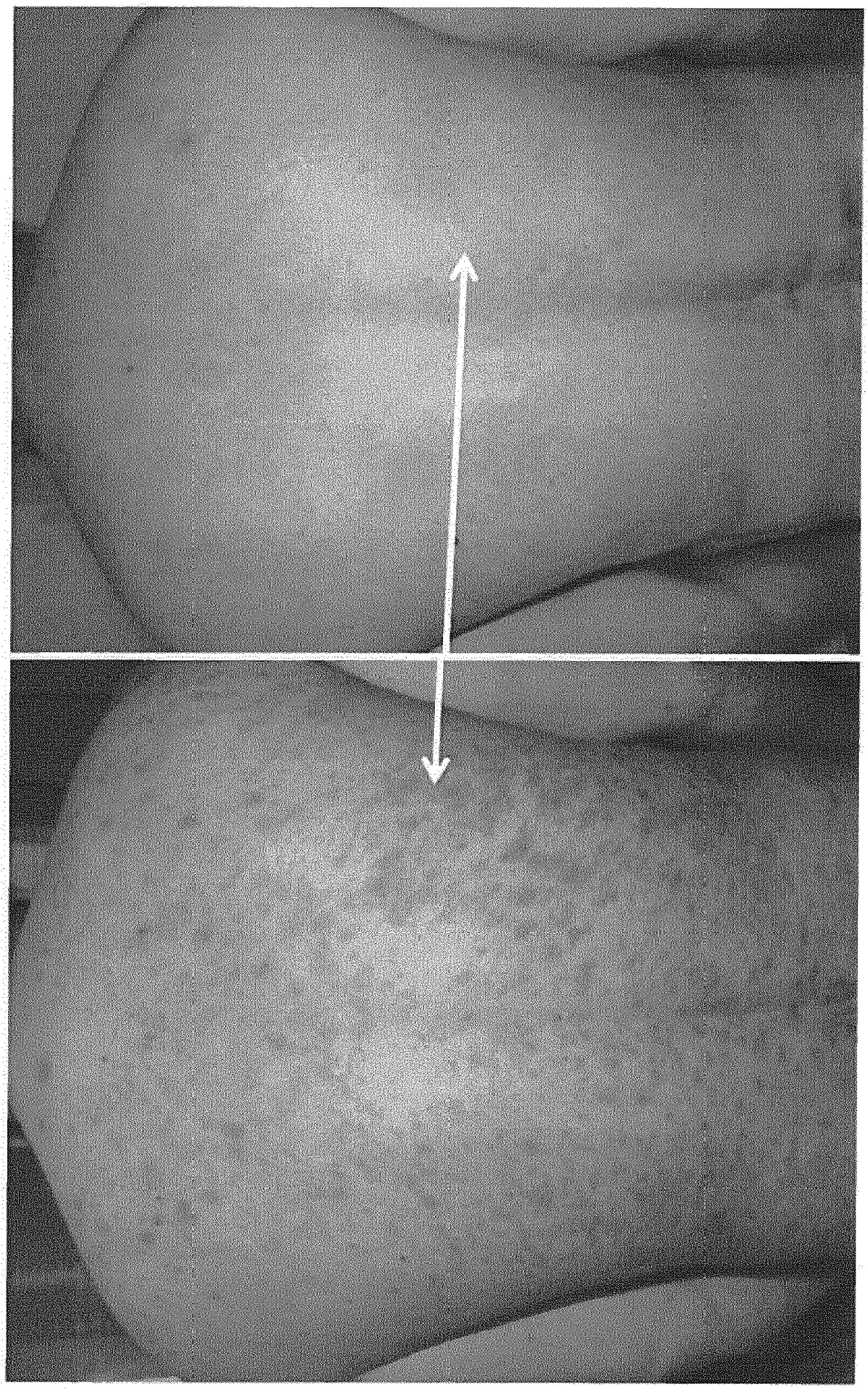
FIG. 3 shows the back area of a male patient suffering from psoriasis before and after two months of treatment with a composition according to the present invention (Recipe P).

Patient C:

A 44 years old male patient suffering from psoriasis received a treatment of the entire body with the composition of Example 2 (Recipe P). 2.5 kg of the composition were used regularly over two months. The patient had already undergone several failed standard treatments. The treatment with the composition of the present invention resulted in a complete abolishment of the symptoms (FIG. 3).

Figure 4:
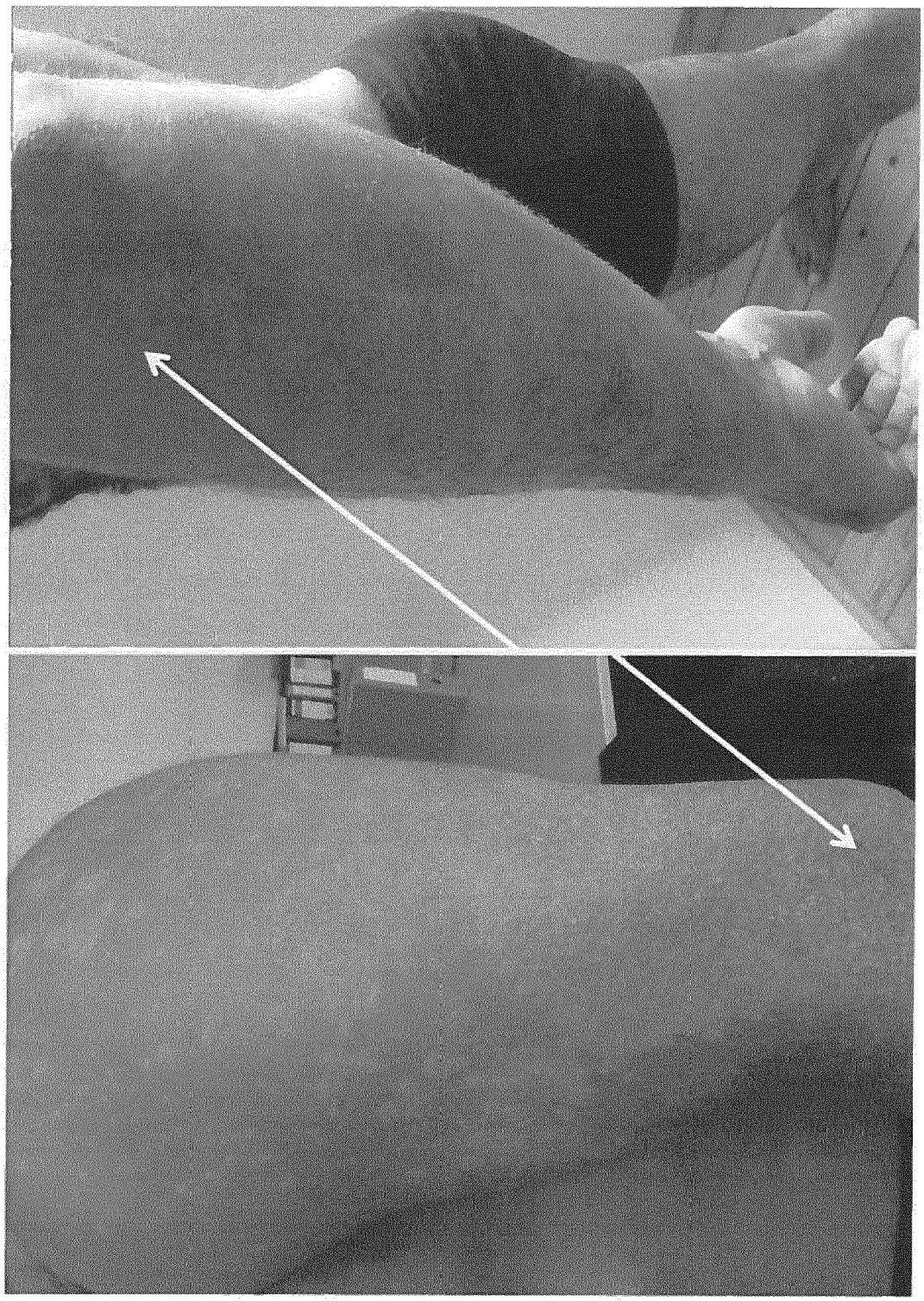
FIG. 4 shows the arm and shoulder area of a male patient suffering from Psoriasis arthritis for more than 12 years before and after two months of treatment with a composition according to the present invention (Recipe P).
Figure 5:
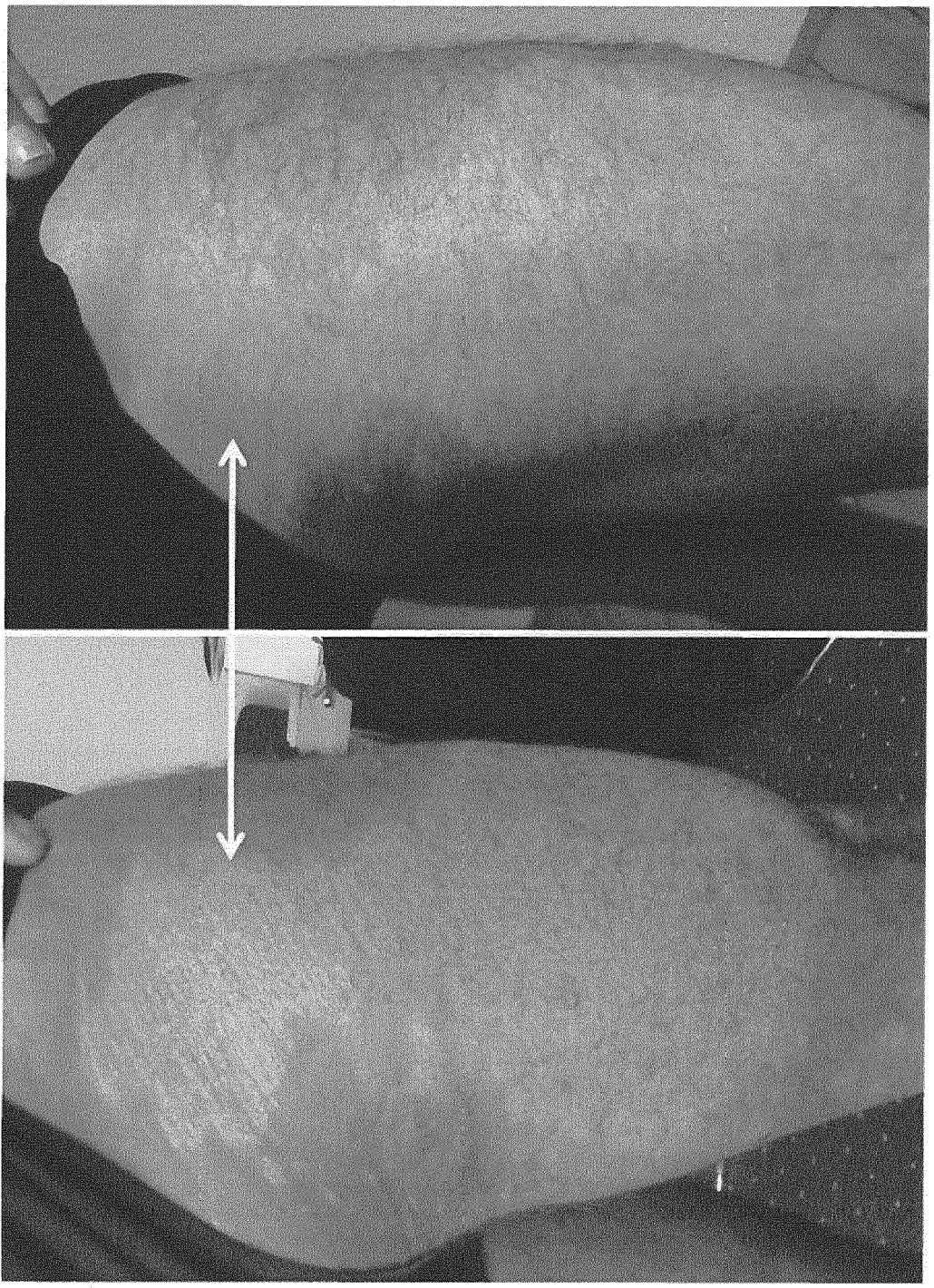
FIG. 5A shows the thigh area of the same patient shown in FIG. 4 before and after two months of treatment with a composition according to the present invention (Recipe P).
FIG. 5B shows the lower leg area of the same patient shown in FIG. 4 before and after two months of treatment with a composition according to the present invention (Recipe P).
Figure 5B:
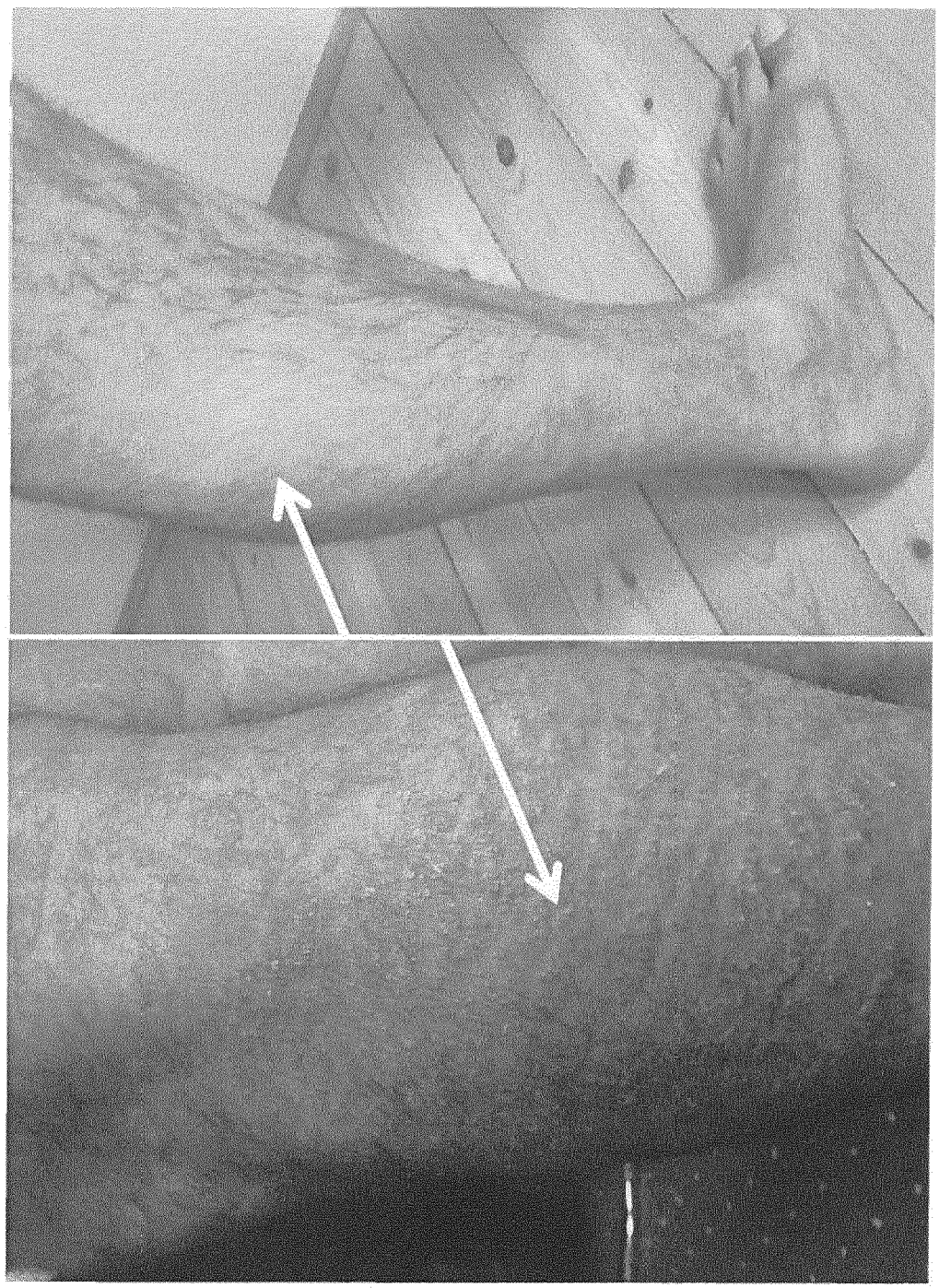

Patient D:

A 34 years old male patient suffering from psoriasis arthritis for more than 12 years received a treatment of the entire body with the composition of Example 2 (Recipe P). The composition was used regularly over two months in an amount of 150 g per day. The patient had already undergone several failed standard treatments, including cortisone treatment. The treatment with the composition of the present invention resulted in a significant amelioration of the symptoms (FIGS. 4, 5A and 5B). This also resulted in a significant positive effect on his psychological well-being.

Example 7

Further Case Reports

Figure 6:
FIG. 6 shows a comparative case involving a 22 years old female patient suffering from atopic eczema from early childhood on, including dryness and severe itching of the affected areas of the skin. The patient received treatment with olive oil two times a week for two months. Although severe itching and redness of the skin resulted from each treatment, the patient continued the treatment. However, after eight weeks the skin remained flaky and dryness even increased.

Patient E (Comparative Study):

A 22 years old female patient suffering from atopic eczema from early childhood on, including dryness and severe itching of the affected areas of the skin, received treatment with olive oil two times a week for two months. Although severe itching and redness of the skin resulted from each treatment, the patient continued the treatment. However, after eight weeks the skin remained flaky and dryness even increased (FIG. 6). Accordingly, the treatment was discontinued.

Figure 7:
FIG. 7 shows a comparative case involving a 4 year old female patient suffering from atopic eczema since birth. The patient received a continuous treatment with black cumin oil for two days. The treatment was discontinued since redness, itching and dryness of the skin increased significantly.

Patient F (Comparative Study):

A 4 years old female patient suffering from atopic eczema since birth received a continuous treatment with black cumin oil for two days. The treatment was discontinued since redness, itching and dryness of the skin increased significantly (FIG. 7).

Figure 8:
FIG. 8 shows a comparative case involving a 43 years old male patient suffering from psoriasis vulgaris affecting the whole body. The patient started a continuous treatment with black cumin oil for six months after several failed therapies with e.g. Daivobet gel. The treatment with black cumin oil yielded no significant results.

Patient G (Comparative Study):

A 43 years old male patient suffering from psoriasis vulgaris affecting the whole body started a continuous treatment with black cumin oil for six months after several failed therapies with e.g. Daivobet gel. The treatment with black cumin oil yielded no significant results (FIG. 8).

Patient H:

A 23 years old male patient suffering from suberythrodermic psoriasis vulgaris with iridocyclitis for 13 years received inpatient treatment to intensify therapy after exacerbation for two weeks and severe itching.

The dermatological diagnosis showed confluent erythematous papules and plaques with medium to large lamelar flaking at the whole integument. Hyperkeratotic plaques were found between the fingers, discreet macerations between the toes, well defined, deeply red foci at the rima ani, and discreet redness at the penis. The psoriasis area and severity index (PASI) at admission was 36.

During inpatient treatment a therapy with fumaric acid was started; the patient further received Ceterizin and Atarax. Itching remained even with Ceterizin treatment. Local treatments included treatment with dithranol vaseline and kopflanette. Further, the whole integument received baths with soft soap and Balneum-Hermal F. The capillitium received Silix washing oil and betamethasone.

The patient further used Curatoderm emulsion for the face. Intertrigines were treated with Candiohermal and Psorcutan ointment. The PASI at discharge was 14.7.

The further medication after discharge from the hospital included fumaric acid, Loratadin, Psorcutan ointment, urea-containing ointment, and Curatoderm emulsions. Nevertheless, the patient showed again exacerbation after four weeks.

Figure 9:
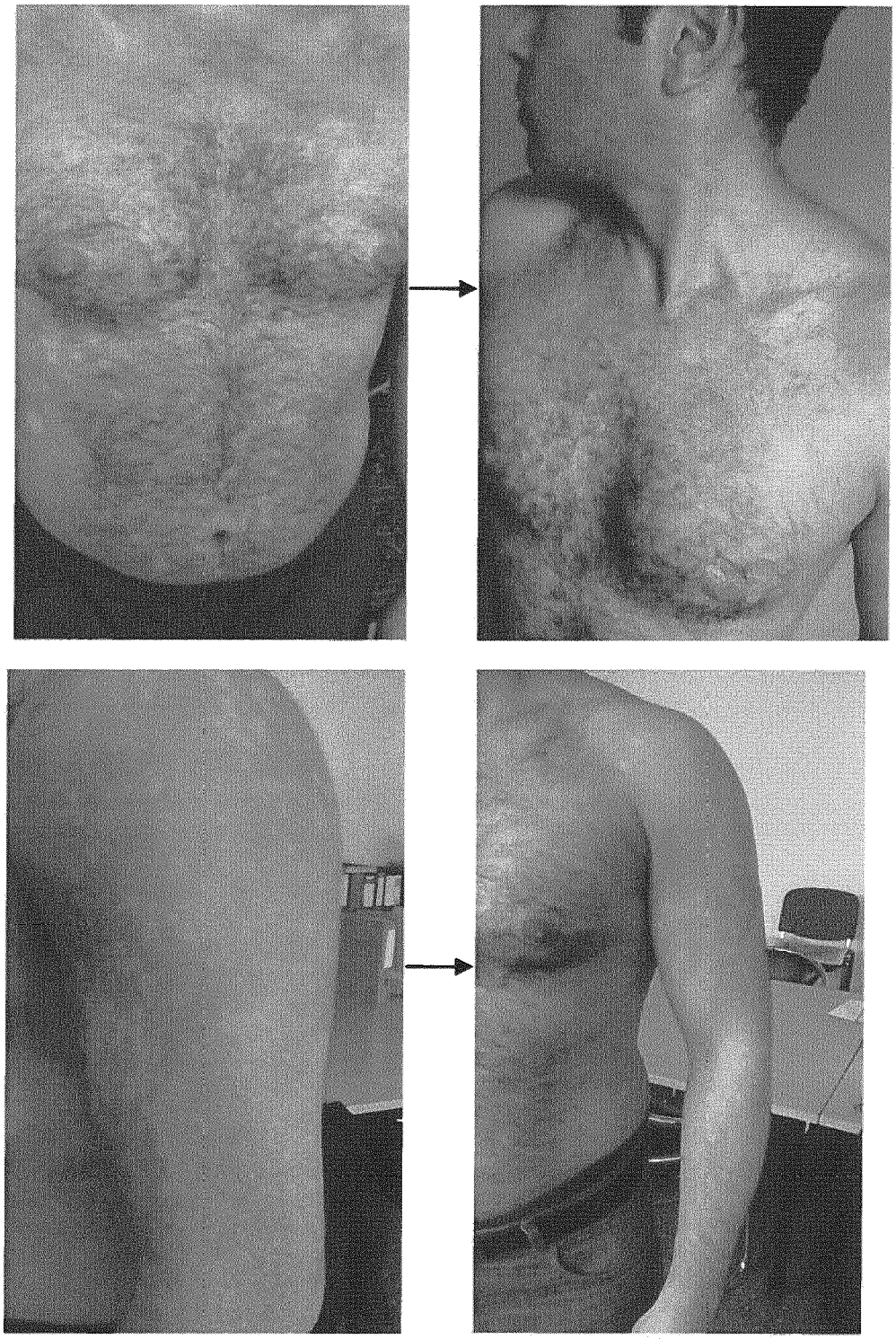
FIG. 9A shows the chest and arm area of a 23 year old male patient suffering from suberythrodermic psoriasis vulgaris with iridocyclitis for 13 years. The patient received continuous treatment with the composition of the present invention (Recipe cf. Example 2) for two months. The success of this treatment was significant.
FIG. 9B shows the heel area of a 23 year old male patient suffering from suberythrodermic psoriasis vulgaris with iridocyclitis for 13 years. The patient received continuous treatment with the composition of the present invention (Recipe cf. Example 2) for two months. The success of this treatment was significant.
FIG. 9C shows the leg area of a 23 year old male patient suffering from suberythrodermic psoriasis vulgaris with iridocyclitis for 13 years. The patient received continuous treatment with the composition of the present invention (Recipe cf. Example 2) for two months. The success of this treatment was significant.
FIG. 9D shows the back and arm area of a 23 year old male patient suffering from suberythrodermic psoriasis vulgaris with iridocyclitis for 13 years. The patient received continuous treatment with the composition of the present invention (Recipe cf. Example 2) for two months. The success of this treatment was significant.
FIG. 9E shows the neck and face area of a 23 year old male patient suffering from suberythrodermic psoriasis vulgaris with iridocyclitis for 13 years. The patient received continuous treatment with the composition of the present invention (Recipe cf. Example 2) for two months. The success of this treatment was significant.
Figure 9B:
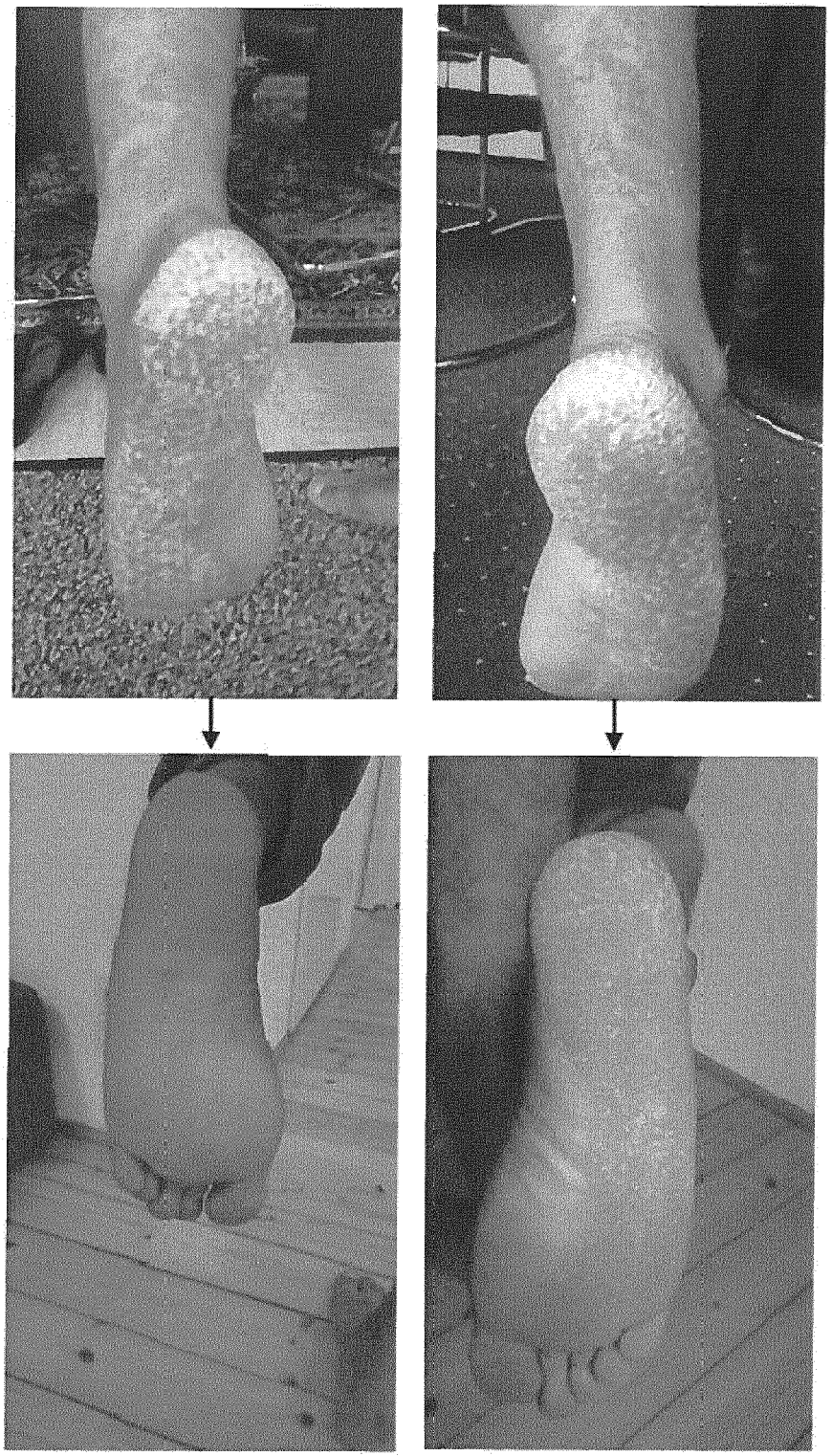
Figure 9C:
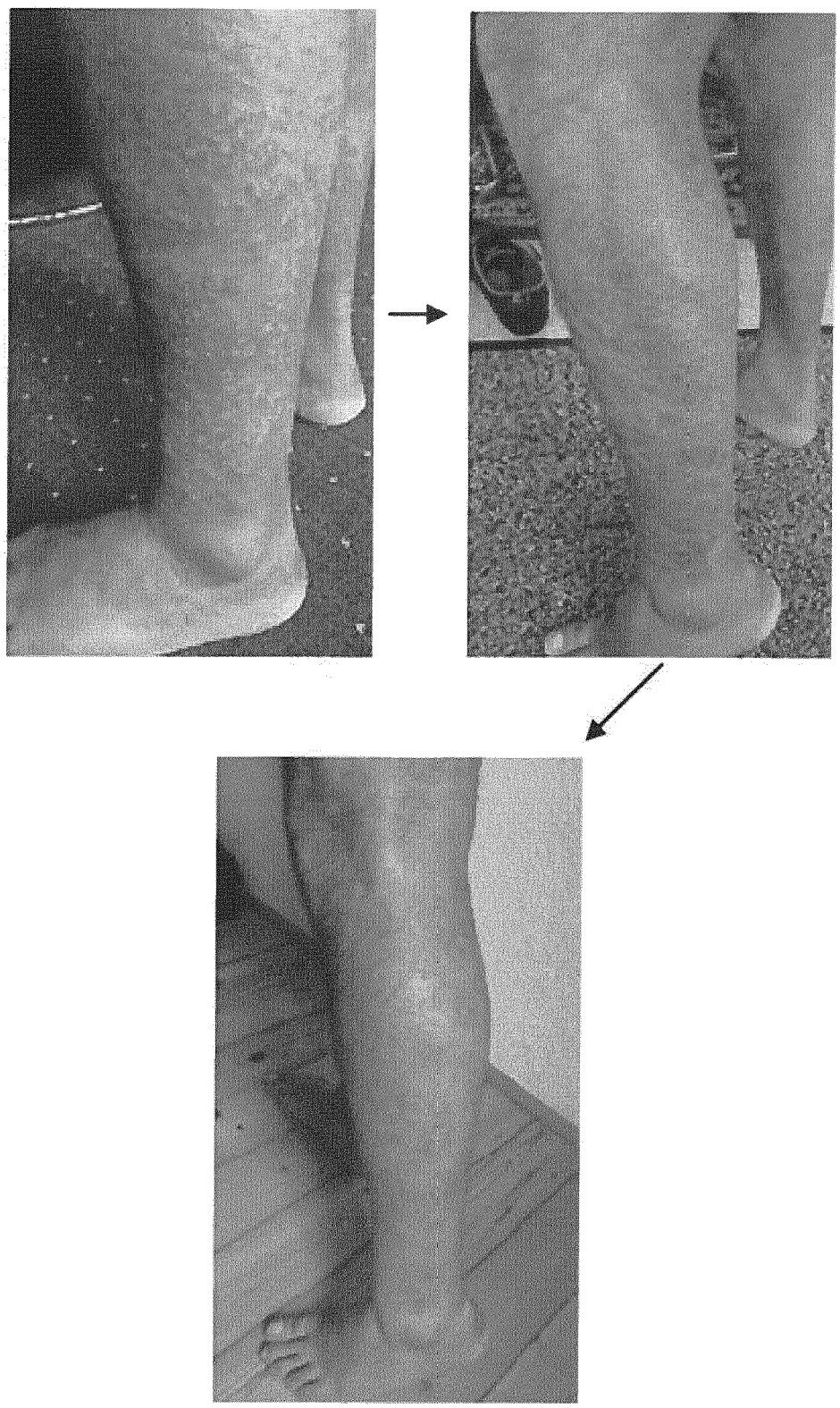
Figure 9D:
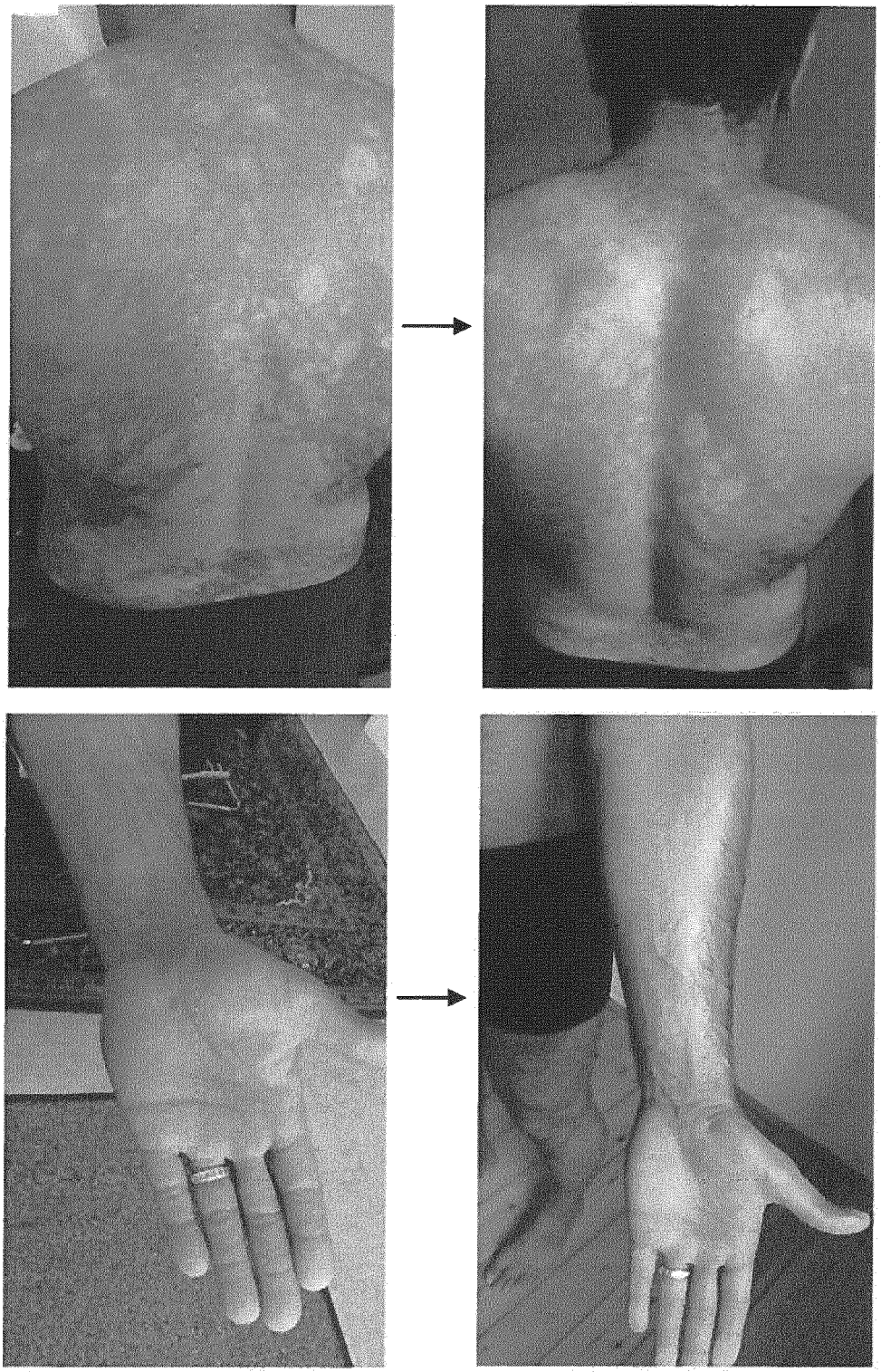
Figure 9E:

This was followed by a continuous treatment with the composition of the present invention (Recipe P; cf. Example 2) for two months. The success of this treatment was significant, as can taken from FIGS. 9 A to 9E.

The invention claimed is:

1. A composition for treating psoriasis or atopic eczema in a human or animal in need thereof consisting essentially of therapeutically effective amounts of:
   a) eucerinum anhydricum;
   b) cocoa butter;
   c) olive oil;
   d) tea tree oil;
   e) vitamin B12 or a derivative thereof selected from the group consisting of cobalamin, hydroxycobalamin, cyanocobalamin, methylcobalamin, adenosylcobalamin, 5'-deoxyadenosyl-cobalamin, aquocobalamin, and nitritocobalamin;
   f) vitamin A or a derivative thereof selected from the group consisting of retinol, retinal, retinyl palmitate, retinyl acetate, retinoic acid, retinoids, beta-carotene, alpha-carotene, gamma-carotene, beta-cryptoxanthene, and retinyl esters; and
   g) black cumin oil.

2. A method for treating psoriasis or atopic eczema in a human or animal in need thereof consisting essentially of topically administering the composition of claim 1 to the human or animal in need thereof.

3. A composition for treating psoriasis or atopic eczema in a human or animal in need thereof consisting essentially of therapeutically effective amounts of:
   a) Base cream DAC;
   b) eucerinum anhydricum;
   c) cocoa butter;
   d) olive oil;
   e) tea tree oil;
   f) vitamin B12 or a derivative thereof selected from the group consisting of cobalamin, hydroxycobalamin, cyanocobalamin, methylcobalamin, adenosylcobalamin, 5'-deoxyadenosyl-cobalamin, aquocobalamin, and nitritocobalamin;
   g) vitamin A or a derivative thereof selected from the group consisting of retinol, retinal, retinyl palmitate, retinyl acetate, retinoic acid, retinoids, beta-carotene, alpha-carotene, gamma-carotene, beta-cryptoxanthene, and retinyl esters; and
   h) black cumin oil.

4. A method for treating psoriasis or atopic eczema in a human or animal in need thereof, the method consisting essentially of topically administering the composition of claim 3 to the human or animal in need thereof.

* * * * *